United States Patent [19]

Delbard

[11] Plant 4,391

[45] Mar. 6, 1979

[54] ROSE PLANT-DELADEL

[75] Inventor: Georges A. Delbard, Paris, France

[73] Assignee: Jackson & Perkins Co., Medford, Oreg.

[21] Appl. No.: 859,996

[22] Filed: Dec. 12, 1977

[51] Int. Cl.[2] ..... A01H 5/00

[52] U.S. Cl. ..... Plt./20

[58] Field of Search ..... Plt./20

*Primary Examiner*—Robert E. Bagwill

*Attorney, Agent, or Firm*—Klarquist, Sparkman, Campbell, Leigh, Hall & Whinston

[57] ABSTRACT

A vigorous well-branched upright plant of the hybrid tea class, having long-lasting flowers of a non-blueing red color, with very strong resistance to Rose Powdery Mildew and slight fragrance.

1 Drawing Figure

The present invention relates to a new and distinct cultivar of rose plant of the hybrid tea class which was originated by me by crossing the cultivar (Super Star × Samourai) with pollen of [Super Star × (Gloire de Rome × Impeccable)].

The primary objective of this breeding was to produce a cultivar of the hybrid tea class suitable both as a garden cultivar and as a greenhouse cultivar for the production of cut flowers, and having a long-lasting flower of a non-blueing red color. This objective was substantially achieved along with other desirable improvements as evidenced by the following unique combination of characteristics which are outstanding in this new cultivar and which distinguish it from its parents as well as from all other cultivars of which I am aware:

1. A vigorous, well-branched and upright plant of approximately five to six feet in the garden under normal cultural practices.
2. A very strong resistance to Rose Powdery Mildew.
3. Foliage, stems and thorns similar in color, form, and size to the cultivar Super Star (Tropicana), U.S. Plant Pat. No. 1,969.
4. A brown, corky surface on irregularly shaped areas of older stems which seem not to be caused by environmental factors and which in no way affects the growth.
5. A very uniform flower color; all of the upper side of the petals, except a very small area at the point of attachment, being near Wilson's Blood Red.
6. A slight fragrance, neither spicy nor sweet.

Asexual reproduction of this new cultivar by budding as performed at Evry, France, and at Wasco, Calif., shows that the foregoing characteristics and distinctions come true to form and are established and transmitted through succeeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose cultivar with color in terminology in accordance with Wilson's Horticultural Color Chart, except where ordinary dictionary significance of color is indicated.

Parentage:

*Seed parent.*—(Super Star × Samourai).

*Pollen parent.*—[Super Star × (Gloire de Rome × Impeccable)].

Classification:

*Botanical.*—Rose hybrid.

*Commercial.*—Hybrid tea.

FLOWER

Observations made from specimens grown in the greenhouse and in the garden at Irvine, Calif., in August of 1977.

Blooming Habit: Continuous.

Bud:

*Size.*—Approximately 1 inch when petals start to unfurl.

*Form.*—Pointed ovoid.

*Color.*—When sepals first divide, slightly darker than Blood Red (820); when half blown, upper side of petals Blood Red (820); lower side of petals near Currant Red (821/2).

*Sepals.*—Color: Outer surface Lettuce Green (861); inner surface covered with white tomentum. Three appendaged sepals lightly appendaged. Two unappendaged sepals, hairy edged.

*Receptacle.*—Color: Lettuce Green (861). Shape: Funnel. Size: Small, slender. Surface: Smooth.

*Peduncle.*—Length: Medium. Surface: Slightly prickly. Color: Lettuce Green (861). Strength: Stiff, erect.

*Opening.*—Outer petals become pointed, center petals lightly recurved.

Bloom:

*Size.*—Medium. Average open size 4" to 4½".

*Borne.*—Singly or several together.

*Stems.*—Long.

*Form.*—When first open, high centered. Permanence: Flattens, outer petals pointed.

*Petalage.*—Number of petals under normal conditions: 30 to 35.

*Color.*—Center of flower: Upper side of petals Blood Red (820). Reverse side of petals near Currant Red (821/2). Base of petals: Very small area of yellow (dictionary significance) encircled by small (⅛") lobes of pink near Geranium Lake (20/2). General tonality from a distance, Blood Red (820).

*Variegations.*—None.

*Discoloration.*—General tonality at end of first day, Blood Red (820); third day, Blood Red (820).

*Fragrance.*—Slight, not sweet or spicy.

Petals:

*Texture.*—Thick, very stiff petal substance.

*Shape.*—Round.
*Form.*—Edges slightly quilled.
*Arrangement.*—Loosely imbricated. Petaloids in center, few.
*Persistence.*—Drop off cleanly.
*Lastingness.*—On the plant, very long. As cut flower, very long.

Reproductive parts:
*Stamens, Anthers.*—Medium. Color, yellow. Arrangement, regular around styles.
*Filaments.*—Color: Yellow, blended with near red.
*Pollen.*—Gold yellow.
*Styles.*—Color: Base is straw yellow; end near stigmas is pink, close to Geranium Lake (20/1). Styles are very hairy.
*Stigmas.*—Amber Yellow (505/1).

PLANT

Form: Bush.
Growth: Very vigorous, upright, branching.
Foliage: Number of leaflets on normal mid-stem leaves: 5 or 7.
*Size.*—Medium.
*Quantity.*—Normal.
*Color.*—New foliage: Near, but lighter than, Garnet Brown (00918/3). Old foliage: Parsley Green (00962/2).

Leaflets:
*Shape.*—Oval pointed. Leaflets often curved with convex upper surface.
*Texture.*—Leathery.
*Edge.*—Serrated.

*Serrations.*—Single, small.
*Petiole.*—Rachis: Color, green. Underside: Prickly.
*Stipules.*—Long, bearded.
*Disease resistance.*—Resistant to mildew under normal growing conditions at Irvine, Calif.

Wood:
*New wood.*—Color: Light green. Bark: Smooth.
*Old wood.*—Color: Green and brown where corky. Bark: Rough or corky.

Prickles:
*Quantity.*—On main stalks from base, many. On laterals from stalk, many.
*Form.*—Long base, hooked downward.
*Color when young.*—Brown.
*Position.*—Irregular.

Small prickles:
*Quantity.*—On main stalk, many. On laterals, many.
*Color.*—Brown.

I claim:

1. A new and distinct cultivar of rose of the hybrid tea class, substantially as herein shown and described, characterized particularly as to novelty by the unique combination of its vigorous, heavily branched plant, a similarity to the cultivar Super Star (Tropicana, U.S. Plant Pat. No. 1,969) of its stems, thorns and foliage, a pronounced resistance to Rose Powdery Mildew, a brown corky surface of irregularly shaped areas on older stems, a very uniform bud and flower color very near to Wilson's Blood Red, and a very slight flower fragrance.

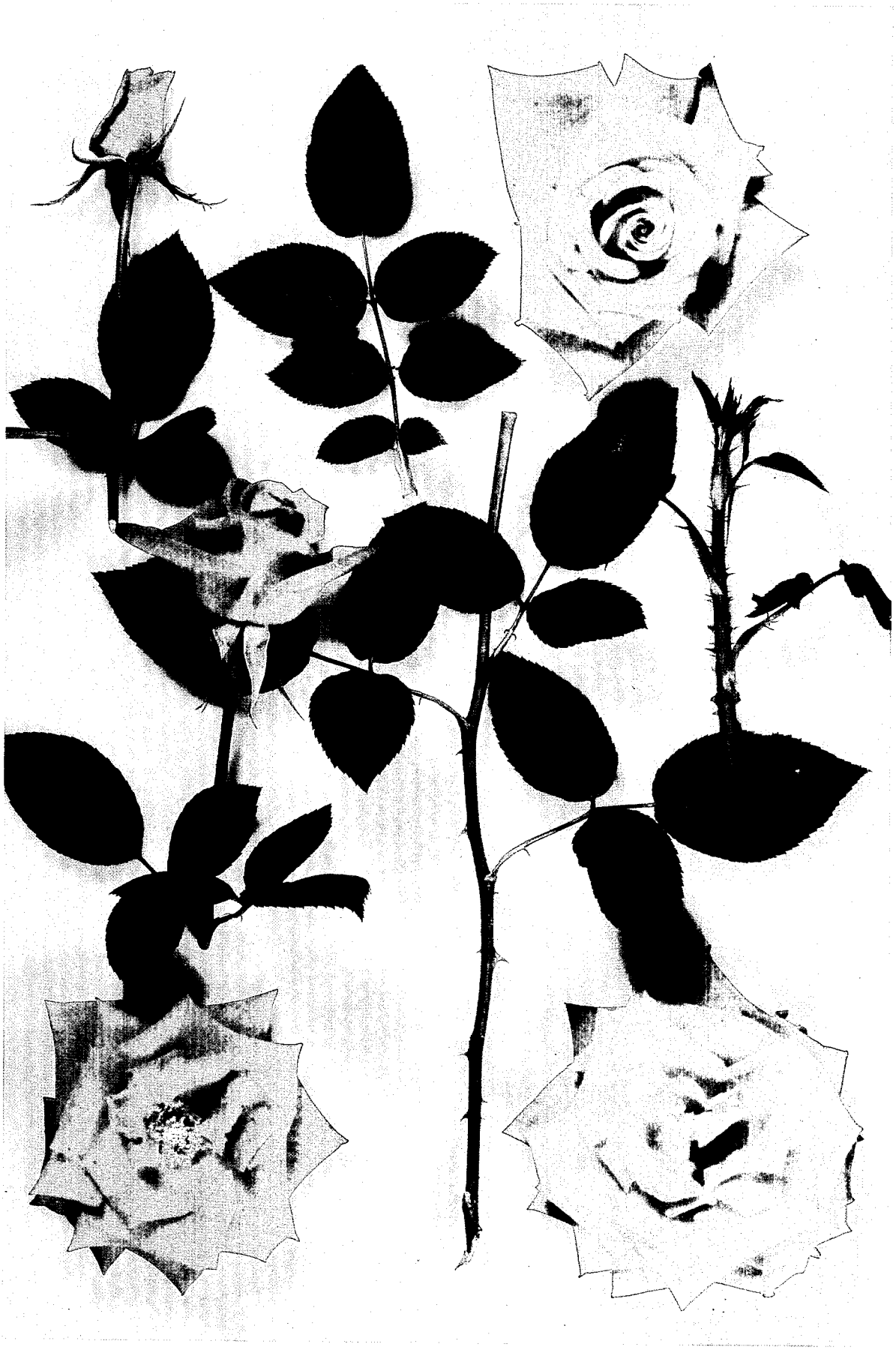

* * * * *